(12) United States Patent
    Kremer

(10) Patent No.: US 6,346,649 B1
(45) Date of Patent: Feb. 12, 2002

(54) PROCESS FOR THE RECOVERY AND RECYCLE OF D-TARTARIC ACID

(75) Inventor: Kenneth Alfred Martin Kremer, Lawrenceville, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/750,253

(22) Filed: Dec. 28, 2000

Related U.S. Application Data

(60) Provisional application No. 60/173,372, filed on Dec. 28, 1999.

(51) Int. Cl.$^7$ .............................................. C07C 59/255
(52) U.S. Cl. ....................................................... 562/585
(58) Field of Search ......................................... 562/585

(56) References Cited

U.S. PATENT DOCUMENTS 4,904,589 A    2/1990    Sato et al.

OTHER PUBLICATIONS

Rutherford, T. et al Eur. J. Inorg Chem (1998)(11) 1677–1688.*
Meixner, A. et al Weinberg Keller (1970), 17(2) 91–6.*
Sawa, Y. K et al. Tetrahedron (1965), 21(5), 1121–8.*
Flassig, E. Osterr Chemiker–Ztg (1956), 57, 308.*

* cited by examiner

Primary Examiner—Paul J. Killos
(74) Attorney, Agent, or Firm—Barbara V. Maurer

(57) ABSTRACT

There is provided a process for the recovery of essentially enantiomerically pure D-tartaric acid from aqueous and organic waste streams generated in the resolution of racemic 2-amino-2,3-dimethylbutyronitrile via the formation and isolation of a crystalline monobasic tartrate salt.

The recovered optically pure D-tartaric acid may be efficiently recycled to provide a sustainable resolution of racemic 2-amino-2,3-dimethylbutyronitrile.

15 Claims, No Drawings

PROCESS FOR THE RECOVERY AND RECYCLE OF D-TARTARIC ACID

This application claims benefit of No. 60/173,372, filed Dec. 28, 1999.

BACKGROUND OF THE INVENTION

Imidazolinone compounds, for instance, those described in U.S. Pat. Nos. 4,188,487; 4,798,619 and 5,334,576, are highly potent, broad spectrum, environmentally benign, herbicidal agents. In general, the herbicidal activity of the R-isomer is approximately 1.8 times that of the racemic imidazolinone compound. Stereospecific processes to prepare chiral imidazolinone herbicidal agents, either directly or indirectly, from (R)2-amino-2,3-dimethylbutyronitrile are described in U.S. Pat. No. 4,683,324 and co-pending patent application Ser. No. 09/304,401, filed on May 3, 1999.

Said nitrile is prepared by a two-step resolution of racemic 2-amino-2,3-dimethylbutyronitrile using D-(−)-tartaric acid as the resolving agent. D-tartatic acid does not occur in abundance in nature, and methods for its production are limited. Although D-tartaric acid is commmercially available, it is expensive and is only available in limited quantities.

Therefore, it is an object of the present invention to provide a process for the recovery of D-tartaric acid from the two-step resolution of racemic 2-amino-2,3-dimethylbutyronitrile.

It is another object of this invention to provide a process for the recycle of said recovered D-tartaric acid in the resolution process.

It is a feature of this invention that the processes provided thereby may be used for repeated recovery and reuse of D-tartaric acid in said two-step resolution.

SUMMARY OF THE INVENTION

The present invention provides a process for the recovery of essentially enantiomerically pure D-tartaric acid from a waste stream containing D-tartrate salts which comprises acidifying said waste stream to a pH of about 2.5 to 4.5 to obtain a crystalline alkali metal hydrogen D-tartrate; and reacting said alkali metal hydrogen D-tartrate with an acid, optionally in the presence of a solvent.

The present invention also provides a process for the recycle of recovered D-tartaric acid in the continuous resolution of racemic 2-amino-2,3-dimethyl-butyronitrile.

DETAILED DESCRIPTION OF THE INVENTION

Imidazolinone compounds such as those described in U.S. Pat. Nos. 4,188,487, 4,798,619 and 5,334,576 are highly potent, broad spectrum, environmentally benign, herbicidal agents. Chiral imidazolinone compounds having the (R) configuration demonstrate an increase in herbicidal activity over the corresponding racemic mixture. The preparation of said chiral compounds by the resolution of racemic 2-amino-2,3-dimethylbutyronitrile, hydrolysis of the resultant (R) 2-amino-2,3-dimethyl-butyronitrile to the corresponding (R)2-amino-2,3-dimethylbutyramide intermediate, and subsequent elaboration of this intermediate to the (R)imidazolinone herbicidal product is described in U.S. Pat. No. 4,683,324. The preparation of chiral imidazolinone compounds having substantially complete retention of enantiomeric purity directly from the (R)aminonitrile starting material to the final chiral imidazolinone herbicidal product is described in co-pending patent application Ser. No. 09/304,401, filed on May 3, 1999.

In general, the two-step resolution described comprises a first resolution step in which racemic 2-amino-2,3-dimethylbutyronitrile (II) in $C_1$–$C_4$ alkanol is treated with D-tartaric acid (I) to afford the D-tartrate salt of (R)2-amino-2,4-dimethylbutyronitrile (III), which crystallizes from solution. Because said aminonitrile partially decomposes in the process of this kinetic resolution, the methanol mother liquor contains varying amounts of ammonium D-tartrate (IV), which is ordinarily discarded. This first resolution step is shown in Flow Diagram I wherein the $C_1$–$C_4$ alkanol is methanol.

FLOW DIAGRAM I

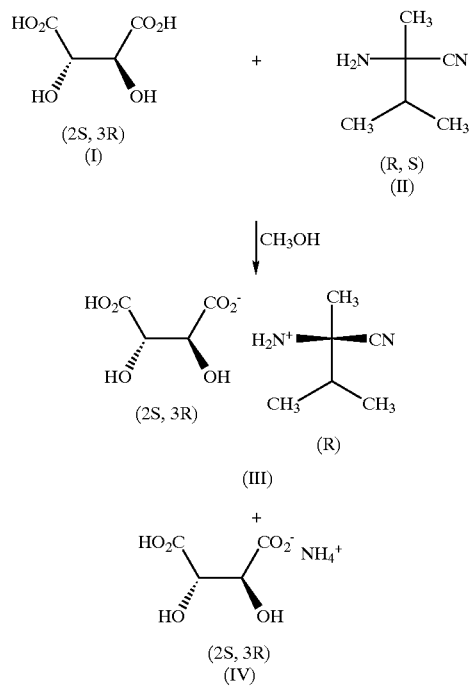

In the second resolution step, (R)2-amino-2,3-dimethylbutyronitrile (VI) is liberated from its D-tartrate salt (III) by treatment with an alkali metal hydroxide in the presence of a minimum amount of water and a water-immiscible solvent, such as toluene. This second resolution step yields an aqueous phase containing a full equivalent of the di(alkali metal) salt of D-tartaric acid (V), which is also ordinarily discarded. This second resolution step is illustrated in flow diagram II wherein M is an alkali metal and the water immiscible solvent is toluene.

FLOW DIAGRAM II

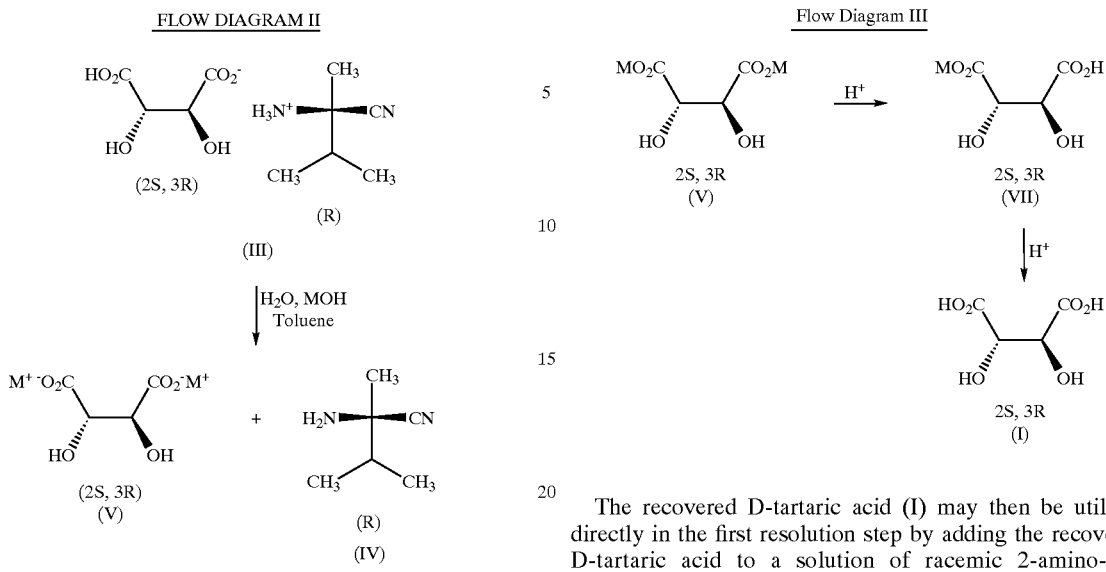

Thus both resolution steps give rise to waste streams containing D-tartrate salts.

Although L-tartaric acid is natural tartaric acid which occurs widely in nature, either as the free acid or in combination with potassium, calcium or magnesium, D-tartaric acid does not occur widely in nature and is commercially available only in limited quantities. Further, existing methods for producing D-tartaric acid are limited. Surprisingly, it has now been found that D-tartaric acid may be recovered in high yield and in essentially enantiomerically pure form from the waste streams produced in the resolution of racemic 2-amino-2,3-dimethylbutyronitrile. Advantageously, the recovered D-tartaric acid may be recycled for use in the same resolution of said aminonitrile. Beneficially, the processes of this invention may be run repetitively, i.e., D-tartaric acid may be repeatedly recovered and recycled in a continuous resolution of racemic 2-amino-2,3-dimethylbutyronitrile, allowing for a sustainable resolution process.

In accordance with the process of the invention the di(alkali metal) D-tartrate or ammonium D-tartrate waste streams produced in the resolution of the above-said aminonitrile are acidified to a pH of about 2.5 to 4.5, preferably 3.0 to 4.0, most preferably about 3.0. The acidification is preferably conducted with hydrochloric or sulfuric acid, to form the crystalline mono-basic hydrogen D-tartrate (VII) and said hydrogen D-tartrate is treated with at least one molar equivalent of an acid, optionally in the presence of a solvent, preferably an aliphatic alkanol, more preferably methanol or ethanol, to give essentially enantiomerically pure D-tartarc acid (I). The process of the invention is illustrated in flow diagram III wherein M is an alkali metal.

The recovered D-tartaric acid (I) may then be utilized directly in the first resolution step by adding the recovered D-tartaric acid to a solution of racemic 2-amino-2,4-dimethylbutyronitrile in a water-immiscible solvent, such as toluene, to yield the corresponding D-tartrate salt (III) as shown hereinabove in flow diagram I.

It is also intended that the processes of this invention embrace the recovery and recycle of L-tartaric acid in a resolution of racemic 2-amino-2,3-dimethyl-butyronitrile to produce (S)2-amino-2,3-dimethylbutyro-nitrile, such as that described in U.S. Pat. No. 4,683,324.

Acids suitable for use in the process of the invention include mineral acids such as hydrogen halides, sulfuric acid, phosphoric acid, or the like, preferably hydrochloric acid or sulfuric acid.

Solvents suitable for use in the inventive process include polar solvents, preferably water miscible. Preferable solvents include aliphatic alkanols such as methanol, ethanol, propanol, isopropanol, or the like, preferably methanol or ethanol, more preferably ethanol.

Alkali metals include sodium, potassium, or lithium, preferably sodium or postassium.

In general, reaction temperatures for the inventive process are directly related to reaction rate, that is increased reaction temperature leads to increased reaction rate. However, excessively high reaction temperatures are to be avoided. Suitable reaction temperatures may be about 0° C. to 50° C., preferably about 5° C. to 35° C., more preferably about 10° to 30° C.

In actual practice, waste streams from a 2-step resolution of racemic 2-amino-2,3-dimethylbutyronitrile, combined or individually, are acidified to a pH of about 3 to form crystalline alkali metal hydrogen D-tartrate and said hydrogen D-tartrate is reacted with at least one molar equivalent of acid, preferably hydrochloric acid or sulfuric acid, optionally in the presence of a solvent, preferably an aliphatic alkanol, more preferably methanol or ethanol, to give the desired essentially enantiomerically pure D-tartartic acid. Advantageously, the crystalline alkali metal hydrogen D-tartrate may be isolated using conventional means such as filtration or, alternatively, may be carried on in the inventive process as is or as a concentrated slurry. Similarly, the recovered D-tartaric acid may be isolated using conventional techniques or recycled as is or as a concentrated slurry.

In order to facilitate a further understanding of the invention, the following examples are presented primarily

EXAMPLE 1

Recovery of D-sodium Hydrogen Tartrate from Aqueous Disodium Tartrate Waste

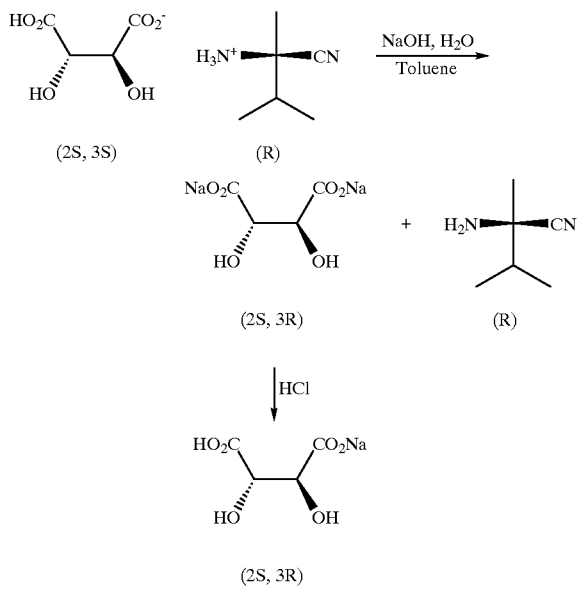

A mixture of (R)-2-amino-2,3-dimethylbutyronitrile (2S, 3S)-tartaric acid salt (89.9 g, 0.34 mmole), toluene, ice and 50% sodium hydroxide (68.5 g, 0.85 mmol) is shaken until no solid particles are observed. The phases are separated and the aqueous disodium tartrate waste produced (343.3 g, 15 wt % D-tartaric acid) is acidified to a pH of about 3 with concentrated hydrochloric acid over a 30 minute period at 8°–13° C., stirred for 15 minutes and filtered. The filtercake is washed with methanol and dried in vacuo to afford recovered D-sodium hydrogen tartrate as an off-white solid 53.2 g (91% recovery) in >99% purity and 100% optical purity as determined by HPLC analysis.

Using essentially the same procedure and employing concentrated sulfuric acid in place of concentrated hydrochloric acid, recovered D-sodium hydrogen tartrate is obtained as an off-white solid (279 g, 77% recovery) >99% purity and 100% optical purity as determined by HPLC analysis.

EXAMPLE 2

Recovery of D-sodium Hydrogen Tartrate from Combined Aqueous Disodium Tartrate and Methanolic Ammonium Tartrate Waste

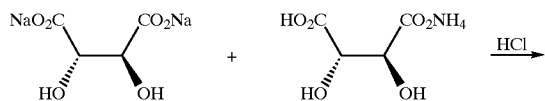

-continued

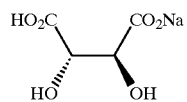

A mixture of aqueous disodium tartrate waste produced as described in Example 1 (438.5 g, 14.5 wt % D-tartaric acid) and a methanolic mother liquor waste slurry of ammonium tartrate (278 g, 2.6 wt % D-tartaric acid) produced as described in U.S. Pat. No. 4,683,324 is acidified to a pH of about 3 with concentrated hydrochloric acid over a 30 minute period at room temperature, stirred for 25 minutes and filtered. The filtercake is washed with methanol and dried in vacuo to afford recovered D-sodium hydrogen tartrate as an off-white solid, 73.7 g, (92% recovery) in >99% purity and 100% optical purity as determined by HPLC analysis.

EXAMPLE 3

Preparation of (R)-2-Amino-2,3-dimethylbutyronitrile (2S,3S)-tartrate from Recovered D-sodium Hydrogen Tartrate

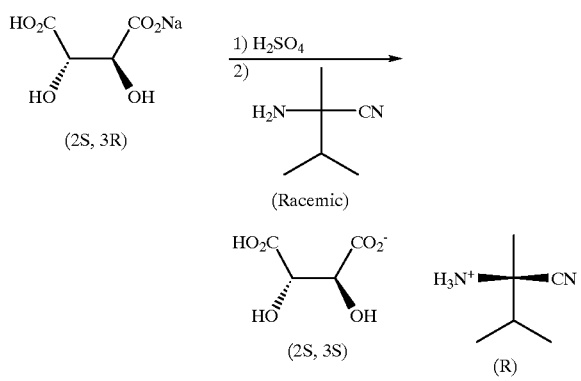

A slurry of recovered D-sodium hydrogen tartrate (20.6 g, 0.119 mol) in methanol is treated with concentrated sulfuric acid (6.1 g, 0.059 mol) at room temperature, stirred for one hour and filtered to remove inorganic salts. A portion of the filtrate is concentrated in vacuo to give a solution of recovered D-tartaric acid (13.6 g, 0.090 mol, 82%) in methanol. This solution is treated with a solution of racemic-2-amino-2,3-dimethylbutyronitrile (12.4 g, 0.11 mol) in toluene, stirred for 16 hours and filtered. The filtercake is washed with methanol and dried to afford (R)-2-amino-2,3-dimethylbutyronitrile (2S,3S)-tartrate, 22.3 g, (61% yield) 95/5 R/S isomer ratio as determined by HPLC analysis.

EXAMPLE 4

Preparation of Crystalline D-tartaric Acid from Recovered D-sodium Hydrogen Tartrate in Ethanol

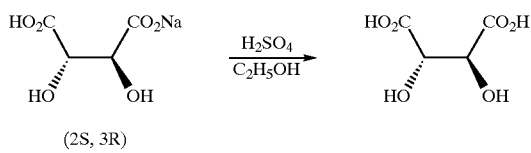

(2S, 3R)

A slurry of recovered D-sodium hydrogen tartrate (50.5 g, 0.293 mol) in ethanol is treated with concentrated sulfuric acid (15.0 g, 0.147 mol) at room temperature, stirred for 45 minutes and filtered to remove inorganic salts. The filtrate is concentrated in vacuo to afford a concentrated slurry of D-tartaric acid in ethanol. The slurry is diluted with toluene and filtered. The filtercake is washed with toluene and dried to afford D-tartaric acid as a crystalline solid, 37.3 g, (83% yield) 97.7% purity 100% optical purity as determined by HPLC analysis.

EXAMPLE 5

Recovery of D-potassium Hydrogen Tartrate from Aqueous Dipotassium Tartrate Waste

(2S, 3R)

Aqueous dipotassium tartrate waste (137.0, 14.7% wt % D-tartaric acid) is acidified to a pH of about 3 with concentrated hydrochloric acid over a 30 minute period at 13–28° C., stirred for about 15 minutes and filtered. The filtercake is washed with methanol and dried in vacuo to afford recovered D-potassium hydrogen tartrate 24,8 g, (98% recovery) in >99% purity as determined by HPLC analysis.

EXAMPLE 6

Preparation of Crystalline D-tartaric Acid from Recovered D-potassium Hydrogen Tartrate in Ethanol

(2S, 3R)    (D)

A slurry of recovered D-potassium hydrogen tartrate (22.1 g, 0.117 mol) in ethanol (148 g) is treated with concentrated sulfuric acid (6.0 g, 0.0588 mol) at room temperature, stirred for 45 minutes and filtered to remove inorganic salts. The filtrate is concentrated in vacuo to a viscous slurry. The slurry is diluted with acetonitrile and filtered. The filtercake is washed with acetonitrile and dried to afford crystalline D-tartaric acid, 4.7 g, (25% recovery), 92.3% purity as determined by HPLC analysis.

What is claimed is:

1. A process for the recovery of essentially enantiomerically pure D-tartaric acid from a waste stream containing D-tartrate salts which comprises acidifying said waste stream to a pH of about 2.5 to 4.5 to obtain a crystalline alkali metal hydrogen D-tartrate; and reacting said alkali metal hydrogen D-tartrate with at least one molar equivalent of an acid, optionally in the presence of a solvent.

2. The process according to claim 1 wherein the alkali metal is sodium or potassium.

3. The process according to claim 1 wherein the acid is a mineral acid.

4. The process according to claim 3 wherein the acid is hydrochloric acid or sulfuric acid.

5. The process according to claim 1 wherein the solvent is methanol or ethanol.

6. The process according to claim 4 wherein the solvent is ethanol.

7. The process according to claim 1 wherein the D-tartrate salt is disodium D-tartrate, dipotassium D-tartrate, ammonium D-tartrate or a mixture thereof.

8. The process according to claim 1 wherein the alkali metal hydrogen D-tartrate is reacted with one molar equivalent of acid.

9. The process according to claim 1 wherein the pH is about 3.0 to 4.0.

10. The process according to claim 9 wherein the pH is about 3.0.

11. A process for the continuous resolution of racemic 2-amino-2,3-dimethylbutyronitrile having D-tartaric acid as resolving agent which comprises the following steps:

a) reacting racemic 2-amino-2,3-dimethylbutyronitrile with D-tartaric acid in the presence of $C_1$–$C_4$ alkanol to give the crystalline D-tartrate salt of (R)-2-amino-2,3-dimethylbutyronitrile and a first waste stream;

b) reacting said D-tartrate salt with an alkali metal hydroxide in the presence of water and a water-immiscible solvent to give (R)-2-amino-2,3-dimethylbutyronitrile and a second waste stream;

c) acidifying said first and second waste streams to a pH of about 2.5 to 4.5 to form a crystalline alkali metal hydrogen D-tartrate salt;

d) reacting said hydrogen D-tartrate salt with at least one molar equivalent of an acid, optionally in the presence of a solvent to give essentially enantiomerically pure D-tartaric acid; and e) reacting said D-tartaric acid according to steps a through d.

12. The process according to claim 11 wherein the pH in step c is about 3.0 to 4.0.

13. The process according to claim 11 wherein the water-immiscible solvent in step b is toluene.

14. The process according to claim 11 wherein the solvent in step d is an aliphatic alkanol.

15. The process according to claim 11 wherein the $C_1$–$C_4$ alkanol is methanol.

* * * * *